United States Patent [19]

Hess

[11] Patent Number: 4,573,473
[45] Date of Patent: Mar. 4, 1986

[54] CARDIAC MAPPING PROBE

[75] Inventor: Stanley R. Hess, Miami, Fla.

[73] Assignee: Cordis Corporation, Miami, Fla.

[21] Appl. No.: 599,950

[22] Filed: Apr. 13, 1984

[51] Int. Cl.[4] .............................................. A61B 5/04
[52] U.S. Cl. .................................... 128/642; 128/696
[58] Field of Search ............... 128/798, 799, 800, 801, 128/784, 639, 640, 642, 696, 699, 700; 604/281, 282

[56] References Cited

U.S. PATENT DOCUMENTS

| | | | |
|---|---|---|---|
| 1,060,665 | 5/1913 | Bell | 604/281 |
| 3,169,528 | 2/1965 | Knox | 604/281 |
| 3,313,293 | 4/1967 | Chesebrough et al. | 128/2.1 |
| 3,380,445 | 9/1965 | Frasier | 128/639 |
| 3,420,223 | 1/1969 | Day | 128/639 |
| 4,044,774 | 8/1977 | Corbin et al. | 128/404 |
| 4,082,086 | 4/1978 | Page | 128/640 |
| 4,125,116 | 11/1978 | Fischell | 128/404 |
| 4,172,451 | 10/1979 | Kline | 128/642 |
| 4,341,221 | 7/1982 | Testerman | 128/642 |
| 4,374,527 | 2/1983 | Iversen | 128/785 |

OTHER PUBLICATIONS

"Effectiveness of Surgical Management of the Wolff--Parkinson-White Syndrome", Will C. Sealy, M.D., *The American Journal of Surgery*, Jun. 1983, vol. 145, 756.

"Selection of Site for Permanent Epicardial Pacing Using Myocardial Testing Electrode", Varriale et al., *New York State Jrnl. of Medicine*, Jul. 1977, 1272.

"Epicardial Mapping in the Wolff-Parkinson-White Syndrome", Gallagher et al., *Circulation*, vol. 57, No. 5, 854, May 1978.

*Primary Examiner*—Kyle L. Howell
*Assistant Examiner*—Daniel Haneiwich
*Attorney, Agent, or Firm*—Henry W. Collins; Thomas R. Vigil

[57] ABSTRACT

The cardiac mapping probe has a soft lead body with a distal end portion containing a pliable, moldable and formable core rod therein. The rod is received within a tubular sheath of the lead body which also includes four insulated wire conductors within the sheath. A head is formed at the distal end of the sheath and has a pad with a flat surface on the underside thereof. Four electrodes are mounted on the flat surface and connected to the wire conductors. Such probe will facilitate placement of the pad flat surface against a section of a heart wall to be mapped and will hold that shape until reconfigured to another shape. Part of the configured, molded shape can provide a handle formation for facilitating gripping and manipulation of the mapping probe.

15 Claims, 7 Drawing Figures

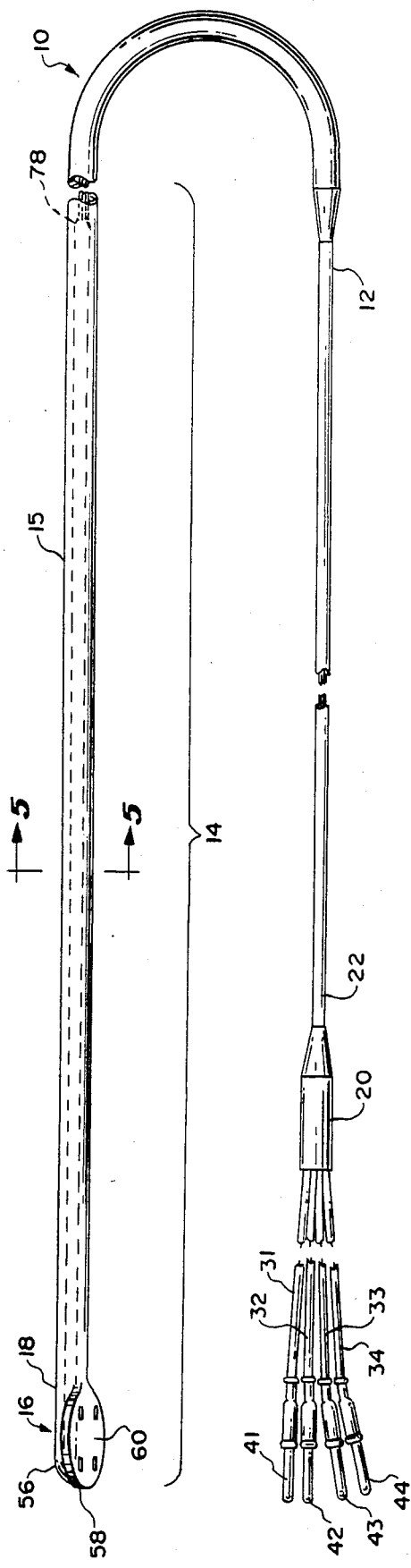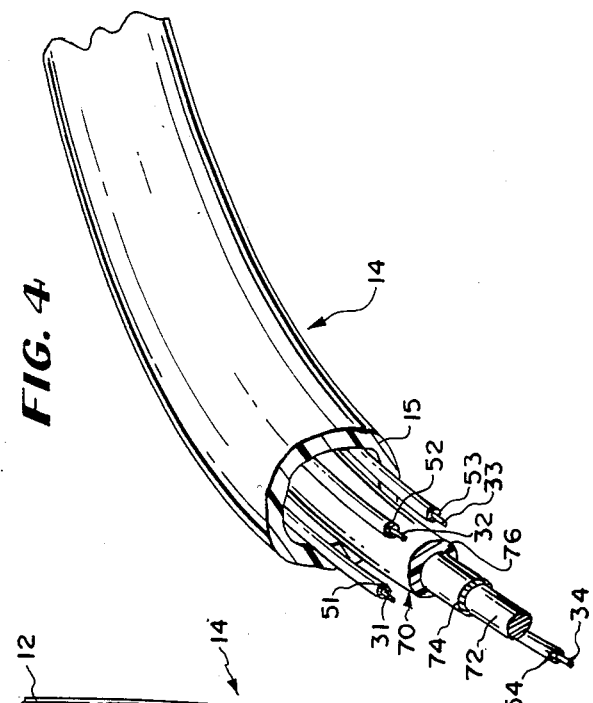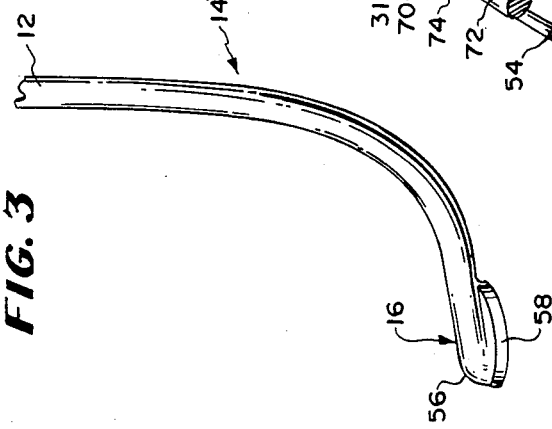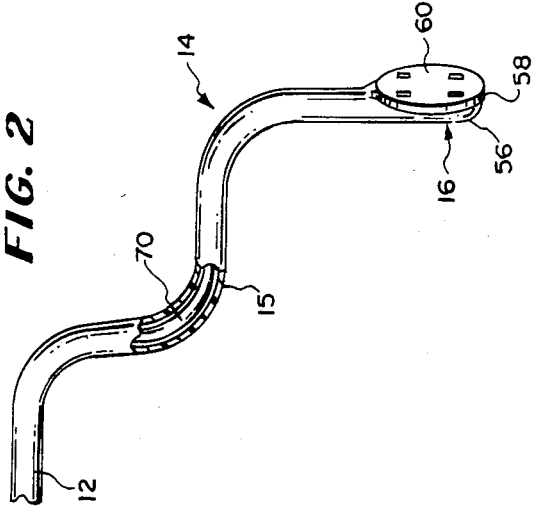

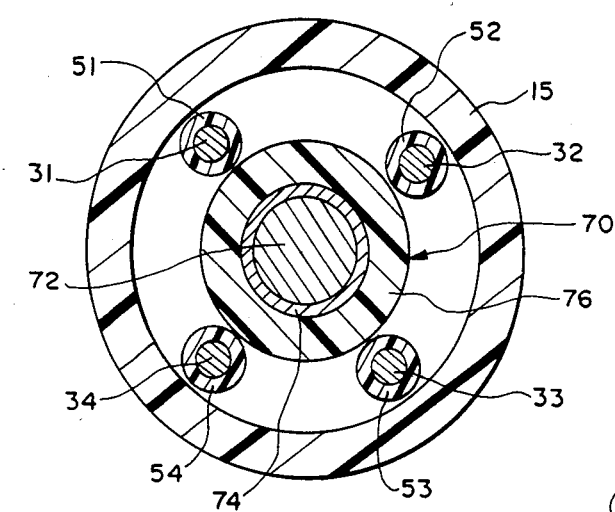
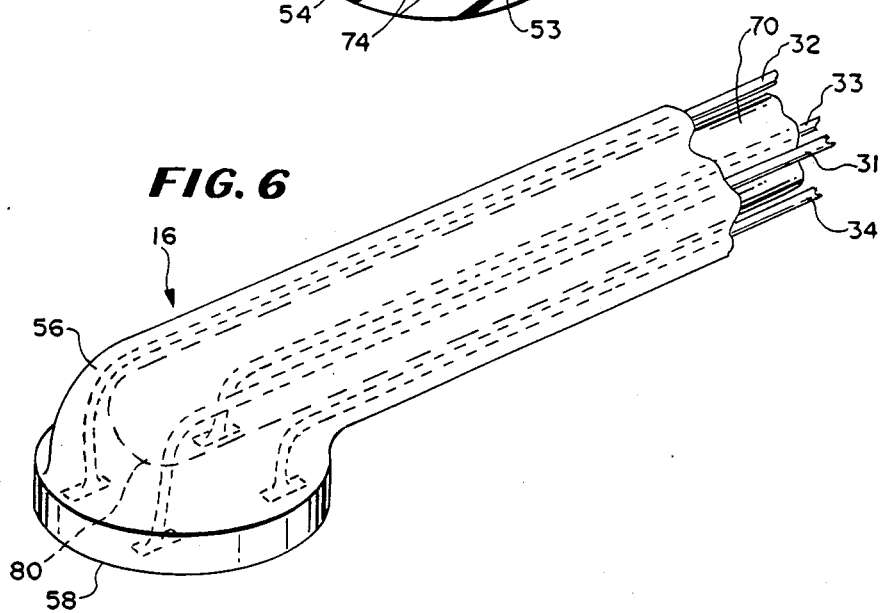
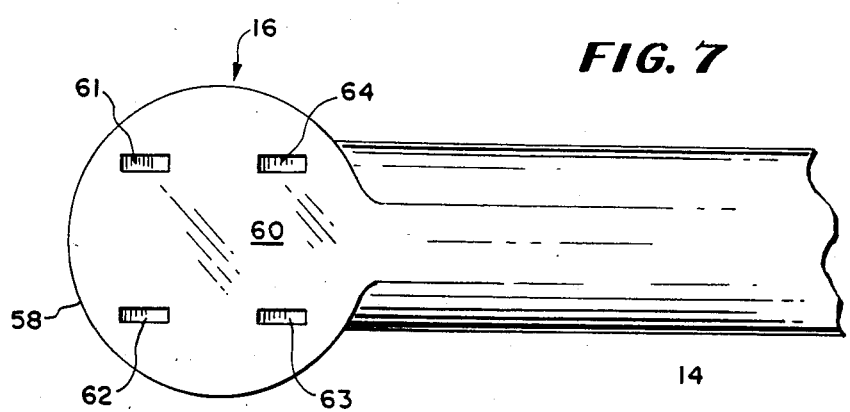

CARDIAC MAPPING PROBE

BACKGROUND OF THE INVENTION

1. Field of the Invention

The present invention relates to a cardiac mapping probe and more particularly to a lead body having electrodes at the distal end thereof which are used in intrasurgical cardiac mapping.

2. Description of the Prior Art

Cardiac mapping is used to locate aberrant electrical pathways within the heart which cause the contractions of the heart muscle to take on peculiar and life threatening contractile patterns.

In the ordinary healthy human heart, contractions begin with a wave of electrical excitation beginning in the right atrium, spreading to the left atrium, and thence to the A-V node which slows down the electrical excitation and then passes it down to what is known as the bundle of His (a bundle of conductive heart muscle fibers) leading into the ventricles. However at times, due to what are generally regarded as congenital anomalies, conductive atrioventricular pathways called accessory pathways of atrioventricular conduction, left over, from the time of embryonic cardiac development, become active in a patient's life. Such pathways, known also as Kent bundles, cause disruption of the normal beat by allowing electrical stimulation of the ventricle to occur through the Kent bundle directly or through re-entry via the Kent bundle into the A-V node at a time inappropriate to the normal cardiac cycle.

Correction of the resultant arythmias or tachicardias is usually accomplished through the surgical disruption of the Kent or His bundle and through the employment of cardiac pacing in some cases.

The only known method for locating Kent bundles is through a procedure called cardiac mapping. Mapping is currently accomplished by dividing the entire ventricular surface of the heart into 53 imaginary sections which are "mapped" electrically using both unipolar and bipolar electrodes and a reference electrode. The unipolar and bipolar electrodes are manually moved about the surfaces of the heart for completely mapping the activation sequence throughout the heart.

There are several different specialized electrodes commonly used for cardiac mapping. By the mere fact of their multiplicity, operating room, surgical and recordation procedures are unnecessarily complicated. A representative group of probes consists of a slightly curved probe, a strongly curved probe and a finger attached set of three bipolar probes, which can, in combination, reach any area of the heart.

Where in certain cases, it is desirable to map an interior portion of the heart, a large incision must be made to facilitate the entry of these probes into the heart. Examples of these probes are illustrated on page 856 of Circulation Volume 57, No. 5, May 1978 in an article devoted to epicardial mapping by Gallagher, et al.

Aside from the complications involved with the above described probes is the concomitant difficulty in manipulating them into and maintaining them in position during mapping. Usually, such probes have only two electrical contact points apiece making determination of the direction and velocity of the flow of activity from a single probe position impossible.

Examples of previously proposed cardiac mapping probes and methods for mapping are disclosed in the following U.S. patents and articles:

| U.S. PAT. NO. | PATENTEE |
|---|---|
| 3,313,293 | J. A. Chesebrough et al |
| 4,044,774 | Terry Corbin et al |
| 4,125,116 | Robert E. Fischell |
| 4,341,221 | Roy L. Testerman |
| 4,374,527 | Alfred A. Iversen |

"Effectiveness of Surgical Management of the Wolff-Parkinson-White Syndrome", Will C. Sealy, M.D., The American Journal of Surgery, June 1983, Vol. 145, 756.
"Selection of Site for Permanent Epicardial Pacing Using Myocardial Testing Electrode", Varriale et al, New York State Jrnl. of Medicine, July 1977, 1272.
"Epicardial Mapping in the Wolff-Parkinson-White Syndrome", Gallagher et al, Circulation, Vol. 57, No. 5, 854, May 1978.

As will be described in greater detail hereinafter, the cardiac mapping probe of the present invention differs from the previously proposed probes by providing a multiple electrode single probe having a lead body which is moldable, pliable and formable into a variety of shapes which it will hold until remolded and reformed.

The single probe design obviates the complicity in surgical and recordation procedures which stem from the extra wiring and sterilization required for a multiplicity of probes. At the same time, the moldable shape of the lead body eliminates the complicated mechanical contortions required to effectively utilize non-shapeable and finger-attached probes for mapping. The shape retention property allows the probe to be inserted through a small incision in the myocardium when necessary while holding its shape once positioned, thus removing the necessity of employing larger, finger-attached probes for the task, with a larger incision.

Furthermore, the lead body has a surface which is soft and pliable and designed to minimize tissue damage, while the distal end thereof has four independently wired electrodes which allow for mapping in a way not contemplated nor provided for in the prior art patents and articles referred to above.

SUMMARY OF THE INVENTION

According to the present invention, there is provided a cardiac mapping probe comprising a lead body having a distal end, a distal end portion and a proximal end and comprising a tubular sheath, a head with a pad having a flat surface mounted at said distal end of said lead body, said pad being located on a side of said tubular sheath such that said flat surface of said pad faces radially outwardly from an elongate axis of said lead body, at least two electrodes on said flat surface of said pad, at least two wire conductors within said tubular sheath and extending the length thereof and being connected to said electrodes, and pliable, moldable means in the form of a ductile metal rod which has a coating thereon to prevent contamination of blood or body tissue with the metal of the rod, which is stiff but bendable, which is rounded at each end to provide said rod without sharp edges and which is mounted within said distal end portion of said lead body for providing said distal end portion with the capability of being formed into various shapes whereby it can be molded and formed into any desired configuration for facilitating holding of said distal end portion and placement of said at least two electrodes against a heart wall and can hold such configuration until remolded and reformed into another configuration.

The cardiac probe of the present invention facilitates cardiac mapping, a procedure preliminary to the correction of accessory atrio-ventricular pathways. In a preferred embodiment the probe comprises a tubular lead body with four leads thereon and a flat ovoid head pad at the distal end thereof. The flat avoid head pad has a flat lower surface or underside having four uninsulated contacts or electrodes for each lead. The head and lead body are constructed of a rubbery silicone or plastic material, e.g. silastic material. A pliable, moldable and formable elongate core rod made of a soft metallic material, preferably a platinum coated copper rod, is encased within a coating of plastic material.

BRIEF DESCRIPTION OF THE DRAWINGS

FIG. 1 is a plan view of the cardiac mapping probe of the present invention and shows the lead body of the probe, the head of the probe having four electrodes at the distal end of the lead body, and lead connectors at the proximal end of the lead body.

FIG. 2 is a perspective view of the distal end portion of the lead body molded to a special shape and shows a portion of the lead body broken away to show an inner pliable, modable and formable core rod.

FIG. 3 is a perspective view of the distal end portion of the lead body molded and formed to another configuration.

FIG. 4 is a fragmentary perspective view of a portion of the distal end portion of the lead body with portions broken away to show parts of the lead body.

FIG. 5 is a sectional view of the lead body distal end portion and is taken along line 5—5 of FIG. 1.

FIG. 6 is an enlarged fragmentary perspective view of the backside of a head at the distal end of the lead body.

FIG. 7 is an enlarged fragmentary plan view of a pad on the frontside of the head at the distal end of the lead body shown in FIG. 6.

DESCRIPTION OF THE PREFERRED EMBODIMENT

Referring now to the drawings in greater detail, there is illustrated in FIG. 1 a plan view of a cardiac mapping probe 10 constructed according to the teachings of the present invention. The cardiac mapping probe 10 includes a lead body 12 having a larger in diameter distal end portion 14. This distal end portion 14 includes a tubular sheath 15 terminating in a head 16 at the distal end 18 of the lead body 12. The sheath 15 is preferably made of a soft, pliable plastic material such as silicone rubber or silastic material.

The lead body 12 further has a coupling member 20 at the proximal end 22 of the lead body 12 which receives four insulated wire conductors 31-34 each of which has a terminal connector 41-44 at the proximal end thereof.

Each of the insulated wire conductors 31-34 has a coating of insulation 51-54 thereon as shown in FIG. 5.

The terminal connectors 41-44 are adapted to be connected to appropriate electric sensing and recording apparatus used in the mapping of electric potentials, impedances or currents at different locations on the exterior wall surface of a heart or the interior wall surface of a chamber of a heart.

The head 16 includes a rounded cylindrical end 56 at and on one side of the distal end 18 of the lead body 12 and a generally oval shaped or circular shaped pad 58 on the underside of the head 16. This pad 58 has a flat planar surface 60 in which are embedded and arranged four electrodes 61-64 which are connected respectively to the wire conductors 41-44. These electrodes 61-64 can be in the shape of small rectangles and are flush with the flat surface 60 of the pad 58.

Alternatively, the electrodes 61-64 can be formed by bringing out a bared wire conductor end portion of each wire conductor 41-44 through a first opening (not shown) in the pad flat surface 60 and then looping that bared wire conductor end portion back into the pad flat surface 60 through a second opening (not shown) spaced from the first opening. Each pair of openings will be preferably arranged at corners of an imaginary rectangle on the flat surface 60 to provide the generally rectangular orientation of the electrodes 61-64 shown in FIG. 7.

In accordance with the teachings of the present invention, the larger in diameter tubular sheath 15 in the distal end portion of the lead body 12 is larger for receiving not only the four insulated wire conductors 41-44 but also a core rod 70 made of a pliable, formable, bendable, moldable material.

In one preferred embodiment, the core rod 70 includes an inner copper core rod 72, a coating 74 of platinum over the copper core rod 72 and an outer coating 76 of an elastomeric plastic material, such as a silastic or silicone rubber material over the platinum coating 74. Preferably, each end 78 and 80 of the inner copper core rod 72 is rounded to provide the copper core rod 72 without sharp edges.

Typically, the core rod 70 extends into the head 16 and above the pad 58 and has a length of at least 5 inches and preferably 6 inches extending rearwardly from the head 16.

The inner diameter of the enlarged tubular sheath 15 of the distal end portion 14 of the lead body 12 is greater than the outer diameter of the core rod 70 to provide space for the insulated wire conductors 41-44.

With the cardiac mapping probe 10 of the present invention formed with a lead body distal end portion 14 having the moldable, pliable, formable, bendable core rod 70 therein, a doctor using the probe can bend the distal end portion 14 of the lead body 12 into whatever configuration he desires and the distal end portion will hold that shape until it is bent or molded into another configuration.

For example, as shown in FIG. 2, the distal end portion 14 of the lead body 12 is shown being bent into two L-shaped curves such as might be desired when inserting the head through a small incision in a heart wall to position the flat surface 60 of the pad 58 against a perpendicular inner side wall area of a heart chamber.

In FIG. 3 is shown a simple L-shaping of the distal end portion 14 of the lead body 12 which would be used for placing the flat surface 60 of the pad 58 against an exposed outer wall of a heart.

It will be appreciated that any variety of shapes can be formed with the distal end portion 14 of the lead body 12 of the probe 10. For example, it may be desirable to form a J-shaped configuration with the flat surface 60 of the pad 58 facing inwardly of the J. This shape would be utilized for positioning the flat surface 60 of the pad 58 on a back wall surface of the exposed heart that faces inwardly into the body.

Also, part of the distal end portion 14 can be configured to serve as a handle for the doctor to grip and hold while making potential measurements.

In using the cardiac mapping probe 10 of the present invention, a doctor would first determine whether he was going to map an exterior wall surface of a heart or an interior wall surface of a heart chamber. If it is the former, he would then, according to established mapping procedure, divide the heart wall into a number of imaginary sections or areas which are usually 53 in number. Then he would bend, mold or form the distal end portion 14 of the lead body 12 of the probe 10 into a first configuration which will facilitate mapping of a first section or area. Next, he would place the flat surface 60 of the pad 58 adjacent that area and make measurements of electric potentials, impedances or currents for use in mapping the electrical sensitivity of various areas of the heart.

The above procedure would be repeated for each other area or section of the heart wall surface to be mapped.

If the interior wall surface of a heart chamber is to be mapped, the physician would first make a small incision in the heart wall to gain access to a desired heart chamber. Then, the steps set forth above would be repeated for the imaginary areas or sections of the wall surface of the heart chamber to be mapped.

From the foregoing description, it will be apparent that the cardiac mapping probe 10 of the present invention has a number of advantages, some of which have been described above and others of which are inherent in the invention. Also, modifications can be made to the cardiac mapping probe 10 of the present invention without departing from the teachings of the present invention. For example, the core rod 70 can be made of other materials besides an inner copper rod 72 coated with platinum 74 and then coated with silicone rubber 76. In this respect, the core rod 70 could be made of a solid material so long as such material is pliable, moldable and formable to any desired shape and yet has the property of holding that shape until reconfigured or molded or formed into another shape.

Also, it will be apparent that the distal end portion 14 of the lead body 12 with the pliable, moldable and formable core rod 70 therein, can be molded or formed to provide a handle in the distal end portion 14 of the lead body 12 by which the physician can grasp the distal end portion 14 for placing the flat surface 60 of the pad 58 adjacent an imaginary section or area of a heart wall to be mapped.

Accordingly, the scope of the invention is only to be limited as necessitated by the accompanying claims.

I claim:

1. A cardiac mapping probe comprising: a lead body having a distal end, a distal end portion and a proximal end and comprising a tubular sheath, a head with a pad having a flat surface mounted at said distal end of said lead body, said pad being located on a side of said tubular sheath such that said flat surface of said pad faces radially outwardly from an elongate axis of said lead body, at least two electrodes on said flat surface of said pad, at least two wire conductors within said tubular sheath and extending the length thereof and being connected to said electrodes, and pliable, moldable means in the form of a ductile metal rod which has a coating thereon to prevent contamination of blood or body tissue with the metal of the rod, which is stiff but bendable, which is rounded at each end to provide said rod without sharp edges and which is mounted within said distal end portion of said lead body for providing said distal end portion with the capability of being formed into various shapes whereby it can be molded and formed into any desired configuration for facilitating holding of said distal end portion and placement of said at least two electrodes against a heart wall and can hold such configuration until remolded and reformed into another configuration.

2. The probe of claim 1 wherein said flat surface has a generally oval extent.

3. The probe of claim 1 wherein said lead body has four insulated wire conductors disposed within said tubular sheath and extending the length thereof and four electrodes on said flat surface of said pad, said electrode being spaced apart in a generally rectangular array on said flat surface.

4. The probe of claim 3 including at least four lead connectors at said proximal end of said lead body connected to respective ones of said insulated wire conductors.

5. A method for cardiac mapping of exterior surfaces of a heart surface using a cardiac mapping probe as defined in claim 3 comprising the steps of: selecting a first area on the exterior surface of the heart; molding and forming the distal end portion of the probe lead body to a configuration that facilitates placement of the distal end with said electrodes in contact with said first area; making potential, electrical measurements in the first area such as impedance measurements or current measurements; and repeating the above steps until the exterior surface has been mapped.

6. A method for mapping of interior surfaces of a heart chamber using a cardiac mapping probe as defined in claim 3 comprising the steps of: making a small incision in the wall of a heart to provide access to the interior of a heart chamber; selecting a first area in the heart chamber; molding and forming the distal end portion of the probe lead body to a configuration that facilitates placement of the distal end with said electrodes in contact with said first area; making potential, electrical measurements in the first area such as impedance measurements or current measurements; and repeating the above steps until the interior surface has been mapped.

7. The probe of claim 1 wherein said electrodes are embedded in and flush with said flat surface of said pad.

8. The probe of claim 1 wherein said metal rod is approximately six inches long.

9. The probe of claim 1 wherein said tubular sheath in said distal end portion of said lead body is of larger diamter than the remainder of said tubular sheath to accommodate said metal rod.

10. The probe of claim 1 wherein said tubular sheath and said pad are made of silicone rubber.

11. A method for cardiac mapping of exterior surfaces of a heart surface using a cardiac mapping probe as defined in claim 1 comprising the steps of: selecting a first area on the exterior surface of the heart; molding and forming the distal end portion of the probe lead body to a configuration that facilitates placement of the distal end with said electrodes in contact with said first area; making potential, electrical measurements in the first area such as impedance measurements or current measurements; and repeating the above steps until the exterior surface has been mapped.

12. A method for mapping of interior surfaces of a heart chamber using a cardiac mapping probe as defined in claim 1 comprising the steps of: making a small incision in the wall of a heart to provide access to the interior of a heart chamber; selecting a first area in the heart chamber; molding and forming the distal end portion of the probe lead body to a configuration that facilitates placement of the distal end with said electrodes in contact with said first area within said heart chamber; making potential, electrical measurements in the first area such as impedance measurements or current measurements; and repeating the above steps until the interior surface has been mapped.

13. The probe of claim 1 wherein said flat surface has a generally circular extent.

14. The probe of claim 1 wherein said metal rod has a distal end portion which extends in said lead body over said pad having said flat surface.

15. The probe of claim 1 wherein said metal rod is a copper rod and said coating comprises an inner platinum coating and an outer coating of plastic material.

* * * * *